United States Patent [19]

Morgan et al.

[11] Patent Number: 6,011,479
[45] Date of Patent: Jan. 4, 2000

[54] PERSONAL CONTINUOUS AIR MONITOR

[75] Inventors: Ronald G. Morgan, Los Alamos; Samuel A. Salazar, Albuquerque, both of N.Mex.

[73] Assignee: The Regents of the University of California, Los Alamos, N.Mex.

[21] Appl. No.: 09/205,490

[22] Filed: Dec. 4, 1998

[51] Int. Cl.[7] .................................................. G08B 17/10
[52] U.S. Cl. ........................ 340/632; 340/573.1; 250/435; 250/370.02
[58] Field of Search ............................. 340/632, 573.1; 250/435, 370.02, 255, 269.2

[56] References Cited

U.S. PATENT DOCUMENTS

| | | | |
|---|---|---|---|
| 4,808,827 | 2/1989 | Woollam | 250/370.02 |
| 4,820,925 | 4/1989 | Balmer et al. | 250/379 |
| 4,975,575 | 12/1990 | Perlman | 250/255 |
| 5,128,539 | 7/1992 | Rodgers et al. | 250/255 |
| 5,235,190 | 8/1993 | Tucker et al. | 250/435 |

*Primary Examiner*—Nina Tong
*Attorney, Agent, or Firm*—Milton D. Wyrick

[57] ABSTRACT

A personal continuous air monitor capable of giving immediate warning of the presence of radioactivity has a filter/detector head to be worn in the breathing zone of a user, containing a filter mounted adjacent to radiation detectors, and a preamplifier. The filter/detector head is connected to a belt pack to be worn at the waist or on the back of a user. The belt pack contains a signal processor, batteries, a multichannel analyzer, a logic circuit, and an alarm. An air pump also is provided in the belt pack for pulling air through the filter/detector head by way of an air tube.

11 Claims, 2 Drawing Sheets

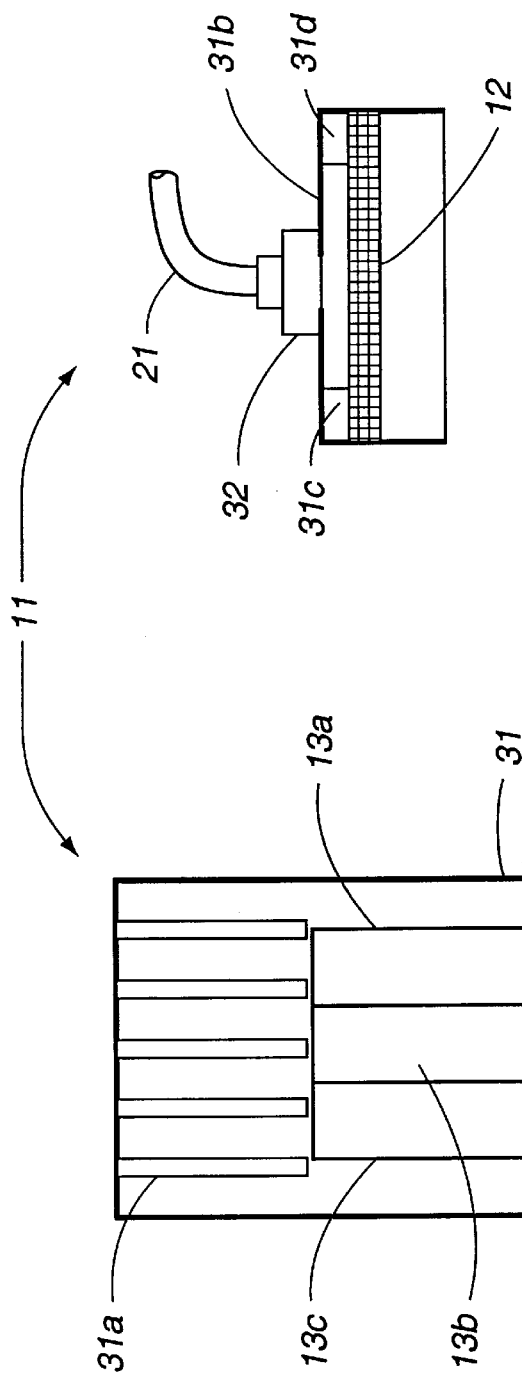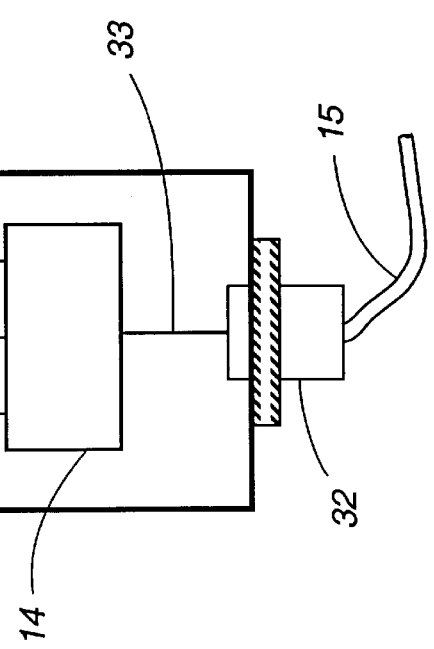

PERSONAL CONTINUOUS AIR MONITOR

The present invention generally relates to radiation monitors, and, more specifically, to airborne radiation monitors to be worn by an individual. This invention was made with Government support under Contract No. W-7405-ENG-36 awarded by the U.S. Department of Energy. The Government has certain rights in the invention.

For workers and other persons who are in certain environments where airborne radioactivity may be present, it is vitally important that the air be constantly monitored for the protection of those persons. Current continuous air monitors (CAMs) are difficult to use in areas that are marginally accessible, such as remote locations where obtaining electrical power is a problem, or physically cramped areas such as pipe chases and tanks. Often a severe condition exists because airflow patterns in these types of environments are not well characterized.

As stated the prior art CAMs, typically require commercial power sources in order to operate. This requirement severely limits their applicability. Oftentimes, the monitoring requirement will be in old, perhaps abandoned facilities, where there is no commercial power available. Thus, they could present a hazard to the health of any investigators who might be in such a situation, by not functioning in such an environment.

Additionally, prior art CAMs have large dilution factors and long response times, making it likely radioactive particles may have been inhaled before any notice of their presence is given. This means there is no way to determine what, if anything, was inhaled prior to the alarm. This ambiguity leads the necessity of nasal smears and possibly bioassay. However, these procedures are not particularly sensitive or accurate, especially at low intake levels.

To avoid such monitoring deficiencies, a monitor that does not require commercial power, and that provides immediate warning of the presence of radiation would be advantageous. Additionally, a monitor personal to the investigator, and which provides monitoring near the point of inhalation, would provide a measure of protection to an investigator far superior to prior CAMs.

It is therefore an object of the present invention to provide apparatus for the personal monitoring of air for radioactivity.

It is another object of the present invention to provide apparatus for the monitoring of radioactivity near the point of inhalation of the user.

It is another object of the present invention to provide apparatus for the monitoring of radioactivity in air that is battery powered.

It is still another object of the present invention to provide apparatus for the monitoring of radioactivity that gives the user immediate notice of radioactivity in the air.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, a personal continuous air monitor capable of sensing radioactivity in the breathing zone of a user comprises a filter capable of trapping radioactive particles, with at least one radiation detector mounted adjacent to said filter capable of outputting electrical signals when radioactivity is present. A preamplifier is connected to said at least one radiation detector for amplifying the output of the at least one radiation detector. Electronic means receive the amplified output from the preamplifier for outputting a signal when a predetermined level of radioactivity has been exceeded. An air pump pneumatically draws ambient air through the filter.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIGS. 3A and 3b are schematical cross-sectional views of the filter/detector head of the present invention.

DETAILED DESCRIPTION

Figure 1:
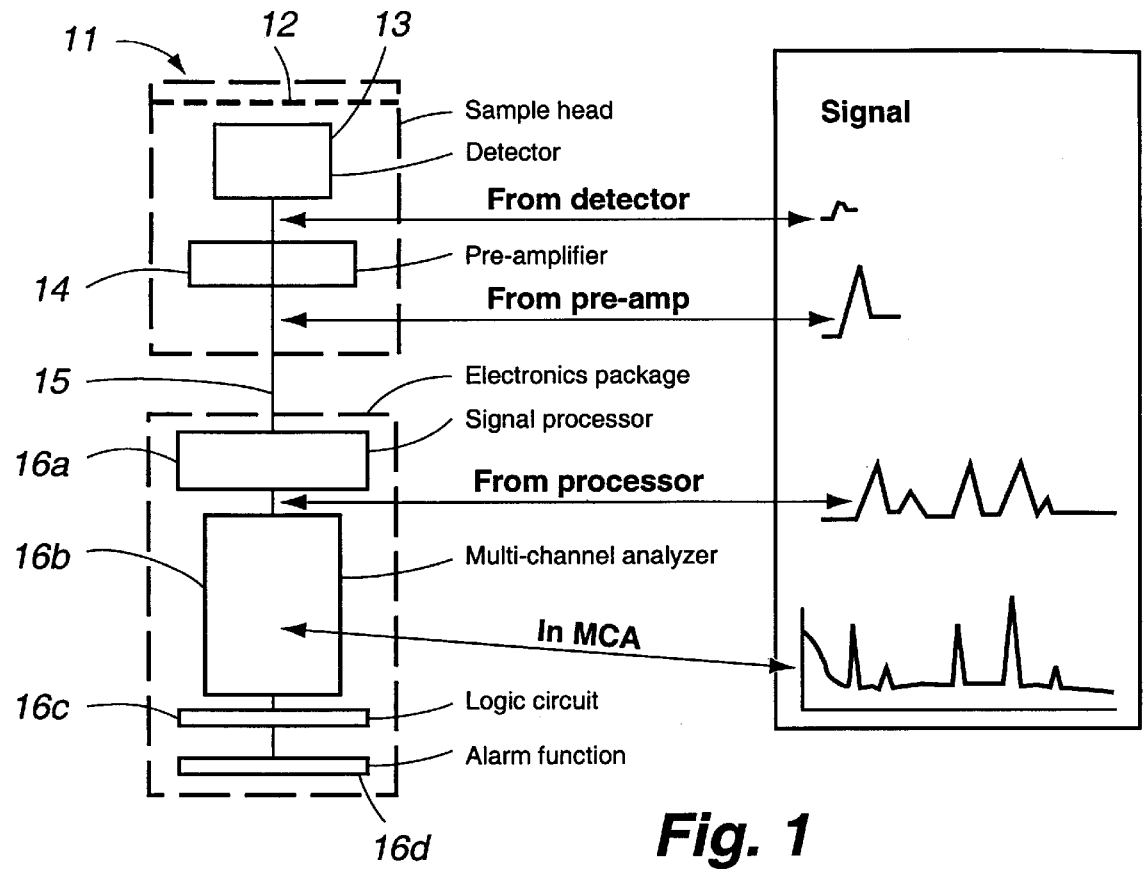
FIG. 1 is a schematic illustration of the components of the present invention and their interconnection.

The present invention provides a personal continuous air monitor that provides real time alarm of radioactivity near the breathing zone of the user. The invention can be most easily understood through reference to the drawing.

In FIG. 1, a schematic illustration of the present invention is presented. Here, it can be seen that filter/detector head 11 contains filter 12, radiation detector 13 and preamplifier 14. Coaxial cable 15 connects preamplifier 14 to signal processor 16a in electronics package 16. The output of signal processor 16a is provided to multichannel analyzer (MCA) 16b. The output of MCA 16b is provided to logic circuit 16c and to alarm 16d that warns the user of the presence of radioactive material.

Filter 12 may be any suitable air filter, such as a membrane or glass fiber filter, depending on the application of the present invention. Appropriate filter material for filter 12 is manufactured by MILLIPORE®. The purpose of filter 12 is to trap particles of radioactive material so that they are detected by radiation detector 13, and to allow off-line testing to investigate any radioactive particles trapped by filter 12.

Radiation detector 13 may contain whatever radiation detectors as are appropriate for a particular application. Any appropriate detectors can be used. Satisfactory operation of the present invention can be had with a QUANTRAD® 500-pna-bnc-ac for alpha particle detector, a TGM zp-1442 for beta/gamma count rate, and a TGM zp-1320 for gamma dose rate. Depending on the detectors used, consideration must be given to providing the required voltages.

Preamplifier 14 is used to amplify the signal from detector 13 in order to overcome any losses encountered in passing through coaxial cable 15 when an alpha detector is used. In this case, radiation detector 13 will output less than 0.1 mV in the presence of radiation. Because of this low output level, the output must be amplified by preamplifier 14 to a level of approximately 10 mV before being launched onto coaxial cable 15, with its associated losses. Preamplifier 14 amplifies the output of an alpha detector to approximately 10 mV, a level high enough to provide a usable signal to signal processor 16a after traversing coaxial cable 15.

In the case of beta and gamma radiation count rate detectors and gamma radiation dose rate detectors, the higher operating voltages produce a higher voltage output. In this case, preamplifier 14 will not be required and can be by-passed.

Figure 2:
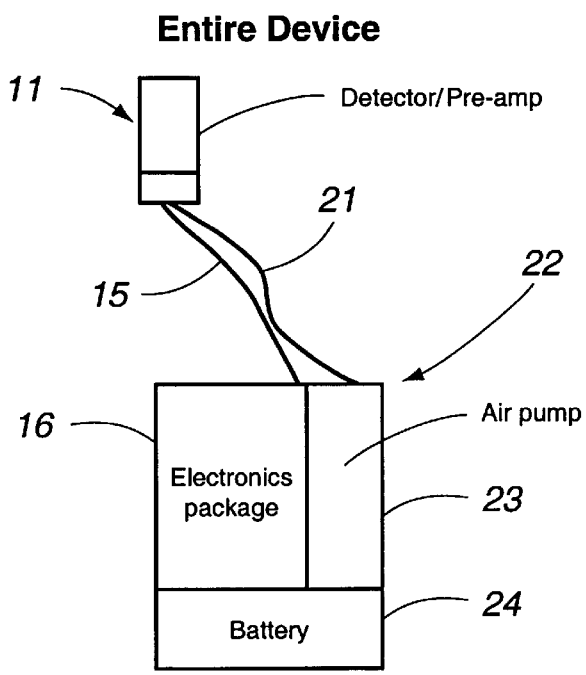
FIG. 2 is a schematic illustration of the interconnection between the filter/detector head and the belt pack of the present invention.

Referring now to FIG. 2, there can be seen belt pack 22 that houses electronics package 16, air pump 23, and battery 24. As seen, air tubing 21, in addition to coaxial cable 15, connects sampler head 11 to belt pack 22. Specifically, air tubing 21 is connected to air pump 23. Air pump 23 and air tubing 21 serve to pull ambient air, including any radioactive materials present in the ambient air, through filter 12. Air pump 23 can be any appropriate air pump capable of moving approximately 2–8 liters of air per minute. One air pump appropriate for use as air pump 23 is manufactured by SKC, Incorporated, as model 224PCXR3.

Battery 24 also is located in belt pack 22. Battery 24 can be one or more batteries capable of providing the energy required by the one or more radiation detectors in detector 13, by electronics package 16, and by air pump 23. For example, an alpha radiation detector in radiation detector 13 requires only approximately 24 V. However, the beta/gamma count rate detectors and gamma dose detectors require wide ranges of voltages, while air pump 23 requires approximately 6 V. Of course, the battery voltage can be stepped up electronically to any desired voltage to serve the needs of detectors 13 and the other electronic components. All of this design is well within the knowledge of those skilled in this art.

As previously stated, electronics package 16 contains signal processor 16a, multi-channel analyzer 16b, logic circuit 16c, and alarm function 16d. Signal processor 16a can be any appropriate signal processor capable of having individual pulses from radiation detector 13 input and outputting waveforms characteristic of the radiation detected and appropriate for input into multi-channel analyzer 16b. Its primary function is to provide a signal to the MCA that is of the appropriate waveform and amplitude required by the MCA.

Multi-channel analyzer 16b is capable of providing discrimination between particular signals provided by signal processor 16. For example, multi-channel analyzer 16b can discriminate between alpha emission from radon and its daughters, and alpha emission from plutonium. Multi-channel analyzer 16b also can discriminate other radiation such as is indicated by a beta/gamma detector.

It should be understood that whether multi-channel analyzer 16b is used depends on the detectors employed in radiation detector 13. That is, if only alpha radiation is being monitored, and there is no concern over alpha emission from radon its daughters, signals from signal processor 16a could be provided directly to logic circuit 16c, bypassing any need for multi-channel analyzer 16b. However, for applications requiring more discrimination, as with beta and gamma radiation, and alpha emission from radon and its daughters, multi-channel analyzer 16b will be necessary.

Logic circuit 16c receives the output of multi-channel analyzer 16b, or, in limited circumstances where only general alpha radiation is to be detected, the output of signal processor 16a. Logic circuit 16c can be any simple logic circuit that is capable of determining when the level of radioactivity as indicated by the output of multi-channel analyzer 16b, or the output of signal processor 16a exceeds a predetermined level.

When the predetermined level of radioactivity has been exceeded, logic circuit 16c outputs a signal to alarm function 16d. In response to this signal from logic circuit 16c, alarm circuit 16c produces the audio and visual signals sufficient to warn the user of the presence of dangerous levels of radioactivity in the area of the user's breathing zone. The nature of such alarms is well within the purview of persons of average skill in this art and is not to be limited to any particular embodiment.

The box on the right side of FIG. 1, titled SIGNAL, symbolically illustrates possible signals from the components of the present invention in response to radiation in the ambient air experienced by a user. The waveforms are intended only to represent the type of output signals from detector 13, preamplifier 14, signal processor 16a, and multichannel analyzer 16b.

Reference should now be directed to FIGS. 3A and 3B, wherein one embodiment of filter/detector head 11 is illustrated in schematical, cross-sectional view. As shown in FIG. 3A, enclosure 31 defines air channels 31a for air passage into enclosure 31. FIG. 3A shows three radiation detectors 13a, 13b and 13c. As previously discussed, the actual radiation detectors employed in filter/detector head 11 will depend on the radiation possibly existing in the area to be investigated. This means that alpha beta and gamma detectors can be installed into filter/detector head 11 in any desired combination. The output of each radiation detector 13a, 13b and 13c is connected to preamplifier 14 for amplification before being launched onto coaxial cable 15. Coaxial cable 15 is connected to preamplifier 14 through cable 33 and coaxial connector 32.

FIG. 3B illustrates the removable end enclosure 31b of filter/detector head 11 that fits over enclosure 31. As seen, removable end enclosure 31b contains filter 12, which is positioned against shoulders 31c and 31d. With removable end enclosure 31b in place on enclosure 31, filter 12 is in close proximity to radiation detectors 13a, 13b, and 13c.

Air pump 23 (FIG. 2) draws air through air hose 21, which is connected to removable end enclosure 31b through fitting 32. With removable end enclosure 31b in place on enclosure 31, air pump 23 will pull ambient air through air channels 31a and through filter 12, leaving any radioactive particles on filter 12 to be detected by radiation detectors 13a, 13b, and 13c. Filter 12 can be easily removed after removal of removable end enclosure 31b when filter/detector head 11 is out of service so that filter 12 can be independently tested to determine the nature of particles trapped thereon while the present invention was in use.

In operation, and with reference to FIG. 2, filter/detector head 11 is worn near the breathing zone of a user, with belt pack 22 attached to a belt or other attachment means at the waist or on the back of the user. When energized, air pump 23 draws air through air channels 31a by way of air hose 21. Any radioactivity in the air will be trapped by filter 12 (FIGS. 1 and 3) and be detected by radiation detector 13. In response, radiation detector 13 will output pulses to preamplifier 14 (FIGS. 1 and 3) for amplification before being launched onto coaxial cable 15, which is attached to electronics package 16 in belt pack 22. In electronics package 16, the amplified pulse is routed to signal processor 16a (FIG. 1) where the waveform is processed to be compatible for the particular multichannel analyzer 16b (FIG. 1) employed. Multichannel analyzer 16b determines the radiation present and outputs its data to logic circuit 16c (FIG. 1). Logic circuit 16c determines whether the data from multi-channel analyzer 16b is above or below some predetermined threshold for radioactivity levels, and, if above the predetermined level, outputs a signal to alarm function 16d, which emits an immediate warning to the user. This warning can be of any type that would render this immediate notice to the user of the presence of dangerous levels of radioactivity.

The foregoing description of the embodiments of the invention have been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A personal continuous air monitor capable of sensing radiation in the breathing zone of a user comprising:
    a filter capable of trapping radioactive particles;
    at least one radiation detector mounted adjacent to said filter capable of outputting electrical signals when radioactivity is present;
    a preamplifier connected to said at least one radiation detector for amplifying said output of said at least one radiation detector;
    wherein said filter, said at least one radiation detector and said preamplifier are located in a first enclosure adapted to be worn in said breathing zone of said user;
    electronic means receive said amplified output from said preamplifier for outputting a signal when a predetermined level of radioactivity has been exceeded; and
    an air pump for pneumatically drawing ambient air through said filter;
    wherein said electronic means and said air pump are located in a second enclosure adapted to be worn at the waist or on the back of said user.

2. The personal continuous air monitor as described in claim 1 wherein said electronic means comprise a signal processor, a multichannel analyzer, a logic circuit and an alarm.

3. The personal continuous air monitor as described in claim 1, wherein said filter comprises a glass fiber filter.

4. The personal continuous air monitor as described in claim 1, wherein said filter comprises a membrane filter.

5. The personal continuous air monitor as described in claim 1 wherein said at least one radiation detector comprises an alpha radiation detector.

6. The personal continuous air monitor as described in claim 1 wherein said at least one radiation detector comprises a beta radiation detector.

7. The personal continuous air monitor as described in claim 1 wherein said at least one radiation detector comprises a gamma radiation detector.

8. The personal continuous air monitor as described in claim 1 wherein said at least one radiation detector comprises an alpha radiation detector and a beta radiation detector.

9. The personal continuous air monitor as described in claim 1 wherein said at least one radiation detector comprises an alpha radiation detector and a gamma radiation detector.

10. The personal continuous air monitor as described in claim 1 wherein said at least one radiation detector comprises an alpha radiation detector, a beta radiation detector and a gamma radiation detector.

11. The personal continuous air monitor as described in claim 1 wherein said at least one radiation detector comprises a gamma radiation detector and a beta radiation detector.

* * * * *